(12) United States Patent
Fukutaki (10) Patent No.: US 10,744,010 B2
(45) Date of Patent: Aug. 18, 2020

(54) SYNTHETIC RESIN STENT

(71) Applicant: JMS CO., LTD., Hiroshima (JP)

(72) Inventor: Shuji Fukutaki, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 8 days.

(21) Appl. No.: 16/070,381

(22) PCT Filed: Jan. 19, 2017

(86) PCT No.: PCT/JP2017/001787
§ 371 (c)(1),
(2) Date: Jul. 16, 2018

(87) PCT Pub. No.: WO2017/126620
PCT Pub. Date: Jul. 27, 2017

(65) Prior Publication Data
US 2019/0015229 A1  Jan. 17, 2019

(30) Foreign Application Priority Data

Jan. 19, 2016  (JP) ................................. 2016-008218

(51) Int. Cl.
*A61F 2/95* (2013.01)
*A61F 2/90* (2013.01)

(52) U.S. Cl.
CPC ......... *A61F 2/90* (2013.01); *A61F 2002/9511* (2013.01); *A61F 2210/0004* (2013.01);
(Continued)

(58) Field of Classification Search
CPC .. A61F 2210/0014; A61F 2/2418; A61F 2/90; A61F 2/95; A61F 2/07;
(Continued)

(56) References Cited

U.S. PATENT DOCUMENTS 5,984,957 A * 11/1999 Laptewicz, Jr. .......... A61F 2/86
606/191
6,569,191 B1   5/2003 Hogan
(Continued)

FOREIGN PATENT DOCUMENTS

CN         102858280 A      1/2013
EP          0897699 A2      2/1999
(Continued)

OTHER PUBLICATIONS

European Patent Office, Search Report issued in the EP Patent Application No. EP17741497.6, dated Jan. 29, 2019, 5 pages.
(Continued)

*Primary Examiner* — Ann Schillinger
(74) *Attorney, Agent, or Firm* — Muncy, Geissler, Olds & Lowe, PC (57) ABSTRACT

Provided is a synthetic resin stent with which it is possible to improve the resistance to pressure applied radially from the outside in a state of expanded diameter even when the fibers are thinned. A synthetic resin stent 1 provided with a stent main body part 2 and a diameter expansion mechanism 3 that connects to the stent main body part 2 and changes the stent main body part 2 from a state of contracted diameter to a state of expanded diameter together with holding the stent main body part 2 in a state of expanded diameter, wherein the diameter expansion mechanism 3 is provided with a ring-shaped member 31 attached to the distal end side of the stent main body part 2, a string-shaped member 32, one end of which is connected to the proximal end side of the stent main body part 2 and inserted through the ring-shaped member 31 and the other end side of which extends to the proximal end side of the stent main body part 2, and a locking part 33 disposed in the vicinity of the connecting portion of the string-shaped member 32 and the stent main (Continued)

body part 2, the locking part 22 being capable of locking the ring-shaped member 31.

4 Claims, 9 Drawing Sheets

(52) U.S. Cl.
CPC .......... *A61F 2210/0014* (2013.01); *A61F 2220/0025* (2013.01); *A61F 2230/0004* (2013.01); *A61F 2230/0069* (2013.01); *A61F 2240/001* (2013.01); *A61F 2250/001* (2013.01)

(58) Field of Classification Search
CPC ........ A61F 2002/011; A61F 2002/9522; A61F 2/013; A61F 2230/0069; A61F 2250/0039; A61F 2250/0067; A61F 2/2436; A61F 2220/0075; A61F 2/844; A61F 2/966; A61F 2/2427; A61F 2/2466; A61F 2250/001
See application file for complete search history.

(56) References Cited

U.S. PATENT DOCUMENTS

| | | | |
|---|---|---|---|
| 6,887,266 B2 * | 5/2005 | Williams | ............... A61F 2/90 623/1.16 |
| 7,704,276 B2 | 4/2010 | Williams et al. | |
| 2007/0026132 A1 | 2/2007 | Williams et al. | |
| 2008/0071356 A1 | 3/2008 | Greenhalgh et al. | |
| 2011/0264186 A1 | 10/2011 | Berglung et al. | |
| 2017/0281376 A1 | 10/2017 | Ide et al. | |

FOREIGN PATENT DOCUMENTS

| | | | |
|---|---|---|---|
| JP | H11-076420 A | | 3/1999 |
| JP | H11-319110 A | | 11/1999 |
| JP | 2001029478 | | 6/2001 |
| JP | 2004517648 A | | 6/2004 |
| JP | 2006-506209 | | 2/2006 |
| JP | 2008-539817 A | | 11/2008 |
| JP | 2009-160079 A | | 7/2009 |
| WO | WO-02/09617 A1 | | 2/2002 |
| WO | WO 2004/045450 A2 | | 6/2004 |
| WO | WO-2011/133277 A1 | | 10/2011 |
| WO | WO 2016/035757 A1 | | 6/2017 |

OTHER PUBLICATIONS

Office Action issued in U.S. Appl. No. 15/507,945, dated Jul. 3, 2018, 10 pages.
Extended European Search Report issued in EP Patent Application No. 15838355.4, dated Mar. 14, 2018, 7 pages.
Office Action issued in CN Patent Application No. 201580046208.X, dated Dec. 26, 2017, 10 pages.

* cited by examiner

SYNTHETIC RESIN STENT

TECHNICAL FIELD

The present invention relates to a synthetic resin stent such as a biodegradable stent.

BACKGROUND ART

Recently, the treatment in which a stent is placed in a stenosis portion to expand the stenosis portion has been performed in stenotic diseases (tumors, inflammation, and the like) of vessels of living organisms such as blood vessels and alimentary canals. As examples of the stent, metallic and synthetic resin stents are known. Among these, metallic stents require a surgical procedure when being removed from the body, and thus, impose a heavy burden on a patient. Therefore, metallic stents are limited to uses in cases when placement is semi-permanent and cases such as malignant tumors in which a surgical procedure has been planned. Due to these circumstances, a biodegradable stent as a synthetic resin stent has been proposed as the stent which is used in cases in which a metallic stent cannot be used.

The biodegradable stent is formed in a cylindrical shape by knitting biodegradable fibers made of synthetic resin, and decomposes in the blood vessels and the alimentary canals over time, and thus, removal of the stent from the body is not necessary. It is expected that the biodegradable stent will alleviate the burden on the patient by being used for, especially, benign stenotic diseases.

A stent, generally, expands the stenosis portion by being brought close to the stenosis portion in a state of contracted diameter and expanding the diameter of the stent. For example, as a method for bringing the biodegradable stent close to the stenosis portion, a method using an endoscope is known. In this method, the stent in a state of contracted diameter is stored in a thin tubular member referred to as a delivery system, and this delivery system is inserted from a forceps port to the inside of the endoscope to bring the stent close to the stenosis portion.

As described above, the stent is brought close to the stenosis portion in a state of contracted diameter and then the stent is expanded in diameter. Meanwhile, when a stent is placed in a stenosis portion and restenosis is caused in the intestinal tract and the like, the stent sometimes reduces its diameter due to the pressure applied radially from the outside. In particular, a biodegradable stent made of synthetic resin fibers has a lower strength compared to a metallic stent, and it is difficult to obtain resistance sufficient to withstand clinical use, against the pressure applied radially from the outside in a state of expanded diameter.

With regard to this type of problem, a technology for providing a biodegradable stent with resistance to the pressure applied radially from the outside by arranging reinforcing beams extending along the axial direction of a cylindrical portion of the biodegradable stent has been disclosed (for example, refer to Patent Document 1).

Patent Document 1: Japanese Unexamined Patent Application, Publication No. 2009-160079

DISCLOSURE OF THE INVENTION

Problems to be Solved by the Invention

However, even with this type of biodegradable stent, it is currently difficult to obtain a sufficient resistance to the pressure applied radially from the outside due to restenosis of the affected part. It is possible to provide the biodegradable stent with resistance to the pressure applied radially from the outside by making the fibers constituting the biodegradable stent thick. However, if the fibers are thick, it becomes difficult for the biodegradable stent to be stored in a thin tubular member such as a delivery system which is used when placing the stent in the stenosis portion.

Thus, the object of the present invention is to provide a synthetic resin stent whose resistance to the pressure applied radially from the outside in a state of expanded diameter can be improved even when the synthetic resin fibers are thinned.

Means for Solving the Problems

The present invention relates to a synthetic resin stent comprising: a stent main body part formed in a cylindrical shape by fibers made of synthetic resin and being deformable from a state of contracted diameter to a state of expanded diameter; and a diameter expansion mechanism that is connected to the stent main body part and deforms the stent main body part from a state of contracted diameter to a state of expanded diameter and holds the stent main body part in the state of expanded diameter, wherein the diameter expansion mechanism comprises: a ring-shaped member attached to a distal end side of the stent main body part; a string-shaped member, one end portion of which is connected to a proximal end side of the stent main body part and inserted through the ring-shaped member, and an other end side of which extends to the proximal end side of the stent main body part; and a locking part disposed at a connecting portion of the string-shaped member and the stent main body part or in the vicinity of the connecting portion and is capable of locking the ring-shaped member; and wherein in a state of the stent main body part being contracted, upon pulling the string-shaped member toward the proximal end side of the stent main body part, the ring-shaped member and the locking part move in approaching directions, and additionally the ring-shape member and the locking part are engaged with each other to hold the stent main body part in the state of expanded diameter.

The locking part is preferably configured by forming a fiber constituting the stent main body part in a loop shape, and one end portion of the string-shaped member is preferably connected to a distal end portion of the locking part formed in a loop shape.

Further, it is preferred that the ring-shaped member is disposed on an inner surface side of the stent main body part, and the string-shaped member has a portion extending on an inner side of the stent main body part on a side where the ring-shaped member is disposed, a portion inserted through the stent main body part in the vicinity of the locking part and a portion extending on an outer side of the stent main body part on a side closer to the locking part than to the portion inserted through the stent main body part.

Furthermore, it is preferred that a plurality of equally spaced diameter expansion mechanisms are disposed in a circumferential direction of the stent body part.

Effects of the Invention

With the synthetic resin stent of the present invention, even when the synthetic resin fibers are thinned, resistance to pressure applied radially from the outside in a state of expanded diameter can be improved.

PREFERRED MODE FOR CARRYING OUT THE INVENTION

Below, a preferred embodiment of the synthetic resin stent of the present invention will be explained with reference to the drawings.

Figure 1:
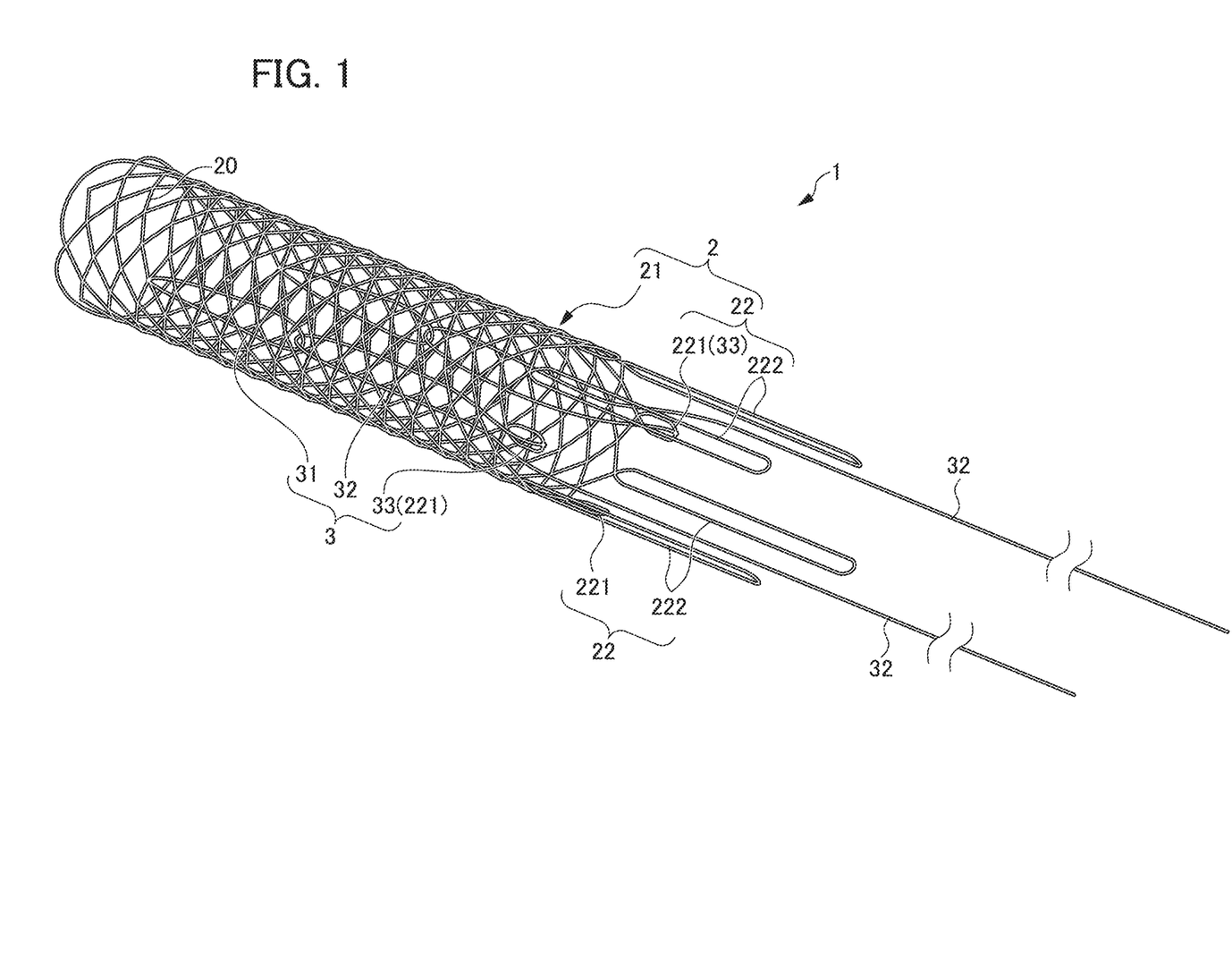
FIG. 1 is a perspective view of the synthetic resin stent according to an embodiment of the present invention.
Figure 2:
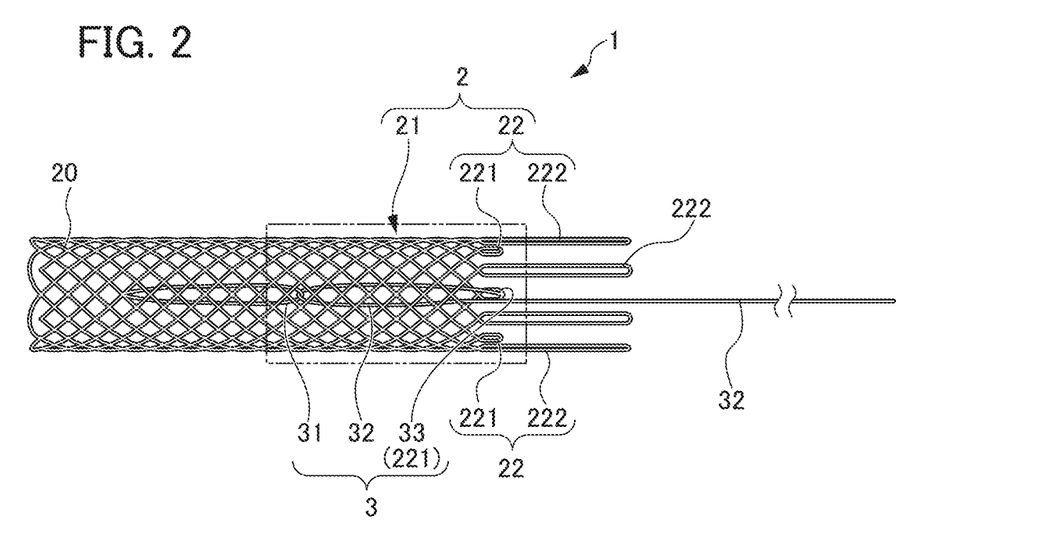
FIG. 2 is a side view of the synthetic resin stent illustrated in FIG. 1.

The synthetic resin stent of the present embodiment is biodegradable stent 1 formed of a biodegradable fiber, comprising stent main body part 2 and diameter expansion mechanism 3 as shown in FIGS. 1 and 2.

Stent main body part 2 is knitted into a cylindrical shape with a plurality of biodegradable fibers and configured to be deformable between the state of contracted diameter and the state of expanded diameter. More specifically, in the present embodiment, stent main body part 2 comprises cylindrical portion 21 and extending portion 22.

Cylindrical portion 21 is formed in a cylindrical shape by knitting a plurality of biodegradable fibers 20 in a mesh shape. Extending portion 22 is formed by a plurality of biodegradable fibers 20 extending from one end side of cylindrical portion 21 toward the outer side in the axial direction of cylindrical portion 21. Specifically, extending portion 22 is formed by one end side of the plurality of biodegradable fibers 20 which constitute cylindrical portion 21 extending toward the outer side in the axial direction of the stent main body part 2 slightly away from the axis.

The distal end portion of extending portion 22 is formed in a loop shape by connecting the ends of the two biodegradable fibers 20. More specifically, the loop-shaped distal end portion is constituted by a portion where the biodegradable fiber 20 is curved at one end of the biodegradable stent 1. Here, "two biodegradable fibers 20" means two biodegradable fibers 20 in the case of focusing only on the extending portion 22, and in the present embodiment, "two biodegradable fibers 20" are derived from one biodegradable fiber 20. In the present embodiment, the extending portion 22 includes a first extending portion 221 having a short extending length and a second extending portion 222 having a longer extending length than the first extending portion 221. A plurality of the first extending portions 221 and the second extending portions 222 are alternately arranged at predetermined intervals in the circumferential direction. In the present embodiment, extending portion 22 is disposed only on one end side of the cylindrical portion 21.

The number of biodegradable fibers forming stent main body part 2 is 24 in the present embodiment, but is not particularly limited. The number of biodegradable fibers is preferably 16 to 24. The size of the stent main body part 2 is not particularly limited, but for example, in the state of expanded diameter, the diameter is 5 to 40 mm and the length is 30 to 150 mm.

The extending length of the first extending portion 221 is preferably 2 mm to 7 mm, and the extending length of the second extending portion 222 is preferably 7 mm to 30 mm.

Biodegradable fiber 20 is not particularly limited as long as it is a biodegradable fiber. Examples of biodegradable fiber 20 include homopolymers, copolymers, and blend polymers thereof synthesized from monomers such as L-lactic acid, D-lactic acid, DL-lactic acid, ε-caprolactone, γ-butyrolactone, δ-valerolactone, glycolic acid, trimethylene carbonate, para-dioxanone, and the like. In particular, it is preferable to use fibers made of poly-L-lactic acid (PLLA) or lactic acid-caprolactone copolymer (P(LA/CL)) or blended polymers thereof.

Biodegradable fiber 20 may be a monofilament yarn or a multifilament yarn. Biodegradable fiber 20 may or may not be twisted. Biodegradable fiber 20 is preferably a monofilament yarn from the viewpoint of strengthening repulsive force against the pressure applied radially from the outside of the stent main body part 2 in the stenosis portion in the living body.

The diameter of biodegradable fiber 20 is preferably 0.05 to 0.7 mm. When the diameter of biodegradable fiber 20 is less than 0.05 mm, the intensity of the biodegradable stent 1 tends to be lowered. When the diameter of biodegradable fiber 20 exceeds 0.7 mm, the diameter in the state of contracted diameter becomes large, so that it tends to be difficult to store the biodegradable stent 1 in a thin tubular member such as a delivery system. It is further preferable that the upper limit of the diameter of biodegradable fiber 20 is 0.3 mm in view of being contained in a delivery system with a thin inner diameter. The lower limit of the diameter of biodegradable fiber 20 is more preferably 0.2 mm from the viewpoint of maintaining high strength.

Figure 3:
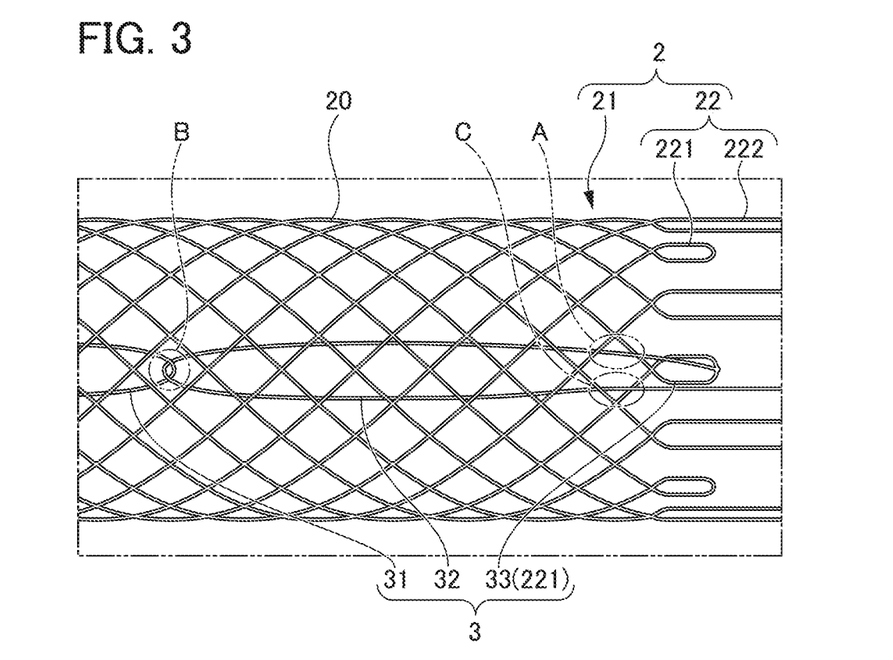
FIG. 3 is a partial enlarged view of FIG. 2, illustrating the diameter expansion mechanism.

Diameter expansion mechanism 3 deforms stent main body part 2 from the state of contracted diameter to the state of expanded diameter, and holds stent main body part 2 in the state of expanded diameter. As shown in FIG. 3, diameter expansion mechanism 3 includes a ring-shaped member 31, a string-shaped member 32 and a locking part 33.

Ring-shaped member 31 is attached to the distal end side of stent main body part 2. More specifically, ring-shaped member 31 is attached in the vicinity of the end portion of the other end side of stent main body part 2 where extending portion 22 is not disposed. Ring-shaped member 31 is composed of a synthetic resin fiber or a biodegradable fiber, and the ends of the synthetic resin fiber or biodegradable fiber are linked to a fiber constituting stent main body part 2 (cylindrical portion 21), so that a ring shape is formed. It is preferable that the attachment position of ring-shaped member 31 to stent main body part 2 is a position close to the distal end portion of stent main body part 2 from the viewpoint of suitably expanding the diameter of stent main body part 2.

One end portion of string-shaped member 32 is connected to the proximal end side of stent main body part 2 and inserted through the ring-shaped member 31, and the other end side extends to the proximal end side of stent main body part 2.

More specifically, in the present embodiment, as shown in FIG. 3, one end portion of string-shaped member 32 is linked and connected to the distal end portion of first extending portion 221. Additionally, string-shaped member 32 runs from the connecting portion with first extending portion 221 on the outer side of stent body part 2, and enters the inner side of cylindrical portion 21 through the mesh of stent main body part 2 (cylindrical portion 21) in the vicinity of first extending portion 221 (see the portion A in FIG. 3).

Next, string-shaped member 32 extends on the inner side of cylindrical portion 21 toward the distal end side of the stent main body part 2, is inserted through ring-shaped member 31, and is then folded back (see portion B in FIG. 3). Next, string-shaped member 32 extends on the inner side of cylindrical portion 21 toward the proximal end side of stent main body part 2, and runs through the mesh of stent main body part 2 (the same mesh as the mesh at which string-shaped member 32 has entered the inner side of cylindrical portion 21 from the outer side) in the vicinity of first extending portion 221 and comes outside cylindrical portion 21 (see portion C in FIG. 3). The other end side of string-shaped member 32 extends to the proximal end side of stent main body part 2.

That is, in the present embodiment, string-shaped member 32 has a portion extending on the inner side of stent main body part 2 (cylindrical portion 21) on a side where the ring-shaped member 31 is disposed, a portion inserted through stent main body part 2 in the vicinity of the connecting portion with first extending portion 221, and a portion extending on the outer side of stent body part 2 on the side closer to first extending portion 221 than to the portion inserted through stent main body part 2. Further, by linking one end portion of string-shaped member 32 to first extending portion 221, first extending portion 221 is connected in a movable state.

Locking part 33 is disposed in the vicinity of the connecting portion between string-shaped member 32 and stent main body part 2. Locking part 33 is constituted in a manner of being capable of locking ring-shaped member 31 by an operation of string-shaped member 32 described below. In the present embodiment, locking part 33 is constituted by first extending portion 221 in which biodegradable fiber 20 constituting stent main body part 2 is formed in a loop shape. String-shaped member 32 is linked and connected to the distal end portion of locking part 33 (first extending portion 221).

It is preferable that in the proximal end portion of first extending portion 221 (locking part 33) to which string-shaped member 32 is connected, the intersection portion of biodegradable fibers 20 is fixed so that one end portion of the linked string-shaped member 32 does not migrate toward the side where the cylindrical portion 21 is disposed.

A plurality of the above-mentioned diameter expansion mechanisms 3 are arranged at equal intervals in a circumferential direction of the stent body part. In the present embodiment, as shown in FIG. 1, two diameter expansion mechanisms 3 are arranged.

According to the above-described diameter expansion mechanism 3, in a state of stent main body part 2 being contracted, upon pulling the string-shaped member 32 toward the proximal end side of the stent main body part 2, the ring-shaped member 31 and locking part 33 move in approaching directions, and the ring-shape member 31 and the locking part 33 are engaged with each other to hold stent main body part 2 in the state of expanded diameter.

Next, the operation of diameter expansion mechanism 3 is described with reference to FIGS. 4 to 7.

As a method of bringing biodegradable stent 1 close to a stenotic portion of a digestive tract or the like, there is a method using an endoscope. In this method, biodegradable stent 1 with the contracted diameter is housed in a thin tubular member which is referred to as a delivery system, and this delivery system is inserted from a forceps port to the inside of the endoscope to bring the stent close to the stenosis portion. In FIGS. 4 to 7, the operation of biodegradable stent 1 is described by omitting the delivery system.

First, biodegradable stent 1 is inserted into a forceps port (not shown) of an endoscope in a state of being housed in a thin tubular member (not shown) such as a delivery system, and is conveyed to a distal end portion of the endoscope. In the present embodiment, biodegradable stent 1 is housed in the delivery system such that the other end side in which ring-shaped member 31 is disposed faces the distal end.

Figure 4:
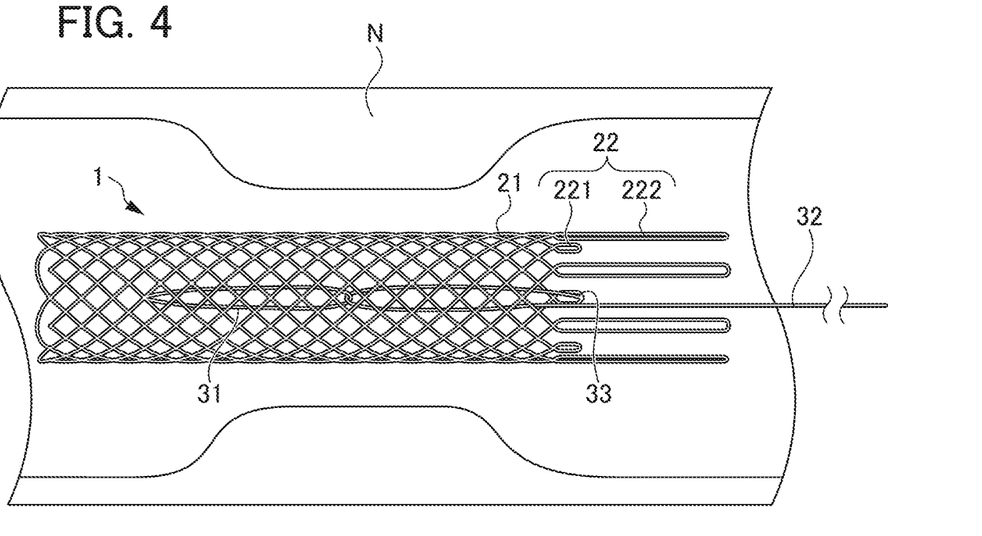
FIG. 4 is a view showing movement of the diameter expansion mechanism, illustrating the stent main body part in a state of contracted diameter.

Next, as shown in FIG. 4, the distal end side of biodegradable stent 1 is discharged from the thin tubular member and disposed at a position surrounded by the stenosis portion N. Stent main body part 2 of biodegradable stent 1 discharged from the thin tubular member expands to some extent. Although not shown, in this state, the other end side of biodegradable stent 1 is held in a state of being disposed inside the thin tubular member, so that the other end side of biodegradable stent 1 is supported by the delivery system.

Figure 5:
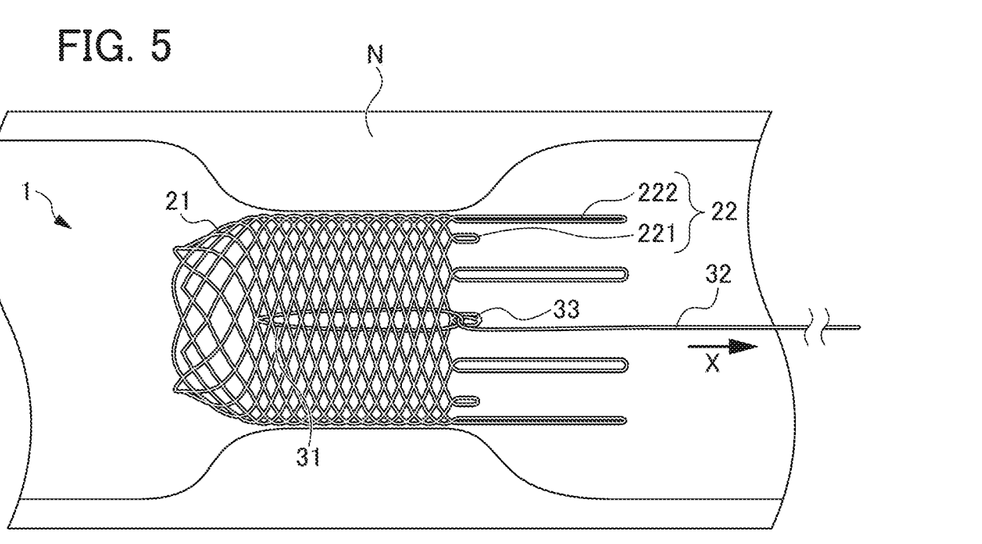
FIG. 5 is a view showing a state of the stent main body part being expanded by pulling the string-shaped member from the state shown in FIG. 4.

Next, as shown in FIG. 5, the other end side of string-shaped member 32 (the side opposite to the one end portion connected to locking part 33) is pulled toward the proximal end side of stent main body part 2 (direction X shown in FIG. 5). Then, ring-shaped member 31 through which string-shaped member 32 is inserted is pulled toward the proximal end side of stent main body part 2 by string-shaped member 32, so that ring-shaped member 31 moves toward locking part 33 side, whereby stent main body part 2 is expanded in diameter and is disposed in the stenosis portion N in a state of expanded diameter. As a result, restenosis of the stenosis portion N can be prevented.

Further, as shown in FIG. 3, string-shaped member 32 runs from the connecting portion with locking part 33 (first extending portion 221) on the outer side of stent main body part 2, enters the inner side of cylindrical portion 21 through the mesh of stent main body part 2 (cylindrical portion 21) in the vicinity of this locking part 33, and extends on the inner side of cylindrical portion 21 toward the distal end side of stent main body part 2. Then, after inserted through the ring-shaped member 31, it is folded back, extends on the inner side of cylindrical portion 21 toward the proximal end side of stent main body part 2, runs through the same mesh as the mesh at which string-shaped member 32 has entered the inner side from the outer side and comes outside cylindrical portion 21. As shown in FIG. 5, this allows ring-shaped member 31 pulled by string-shaped member 32 to run through the mesh in the vicinity of locking part 33 and come out of the inner side to the outer side of stent main body part 2.

Figure 6:
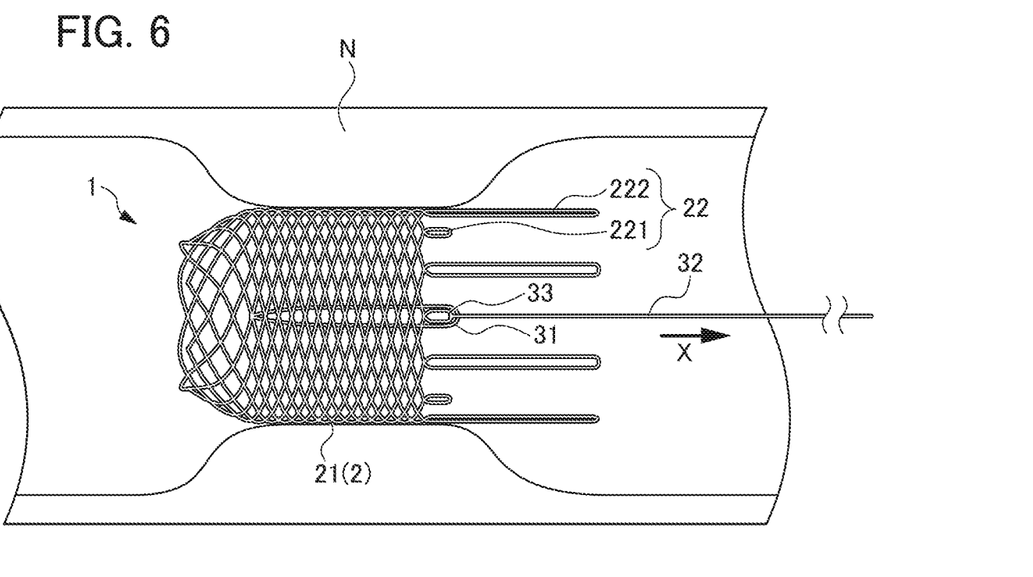
FIG. 6 is a view showing a state of the ring-shaped member being engaged with the locking part by further pulling the string-shaped member from the state shown in FIG. 5.
Figure 7:
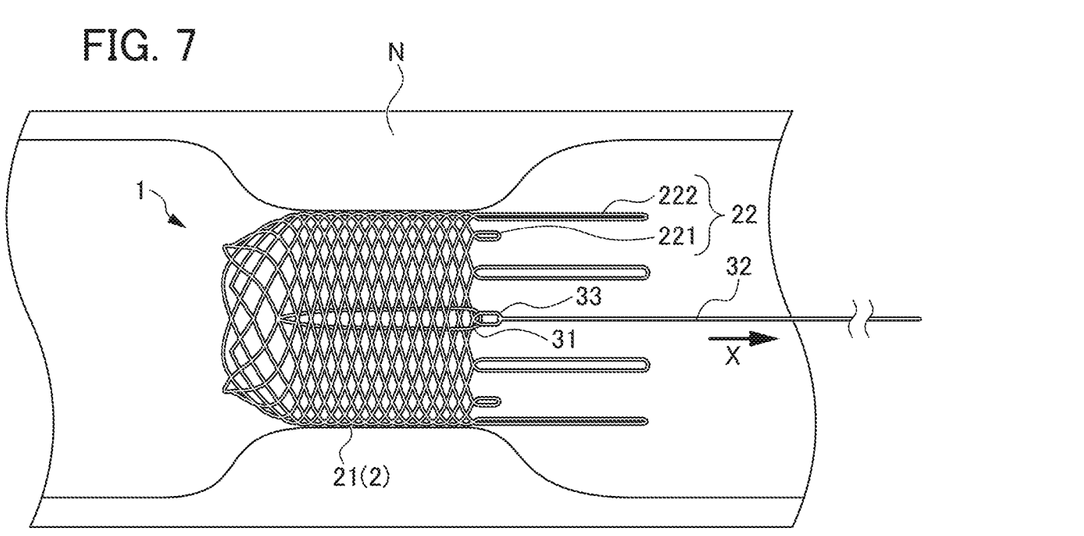
FIG. 7 is a view showing a state of the ring-shaped member being engaged with the locking part by further pulling the string-shaped member from the state shown in FIG. 6.

Next, upon further pulling string-shaped member 32 toward the proximal end side (direction X shown in FIG. 5) of stent main body part 2, ring-shaped member 31 runs over locking part 33 formed in the loop shape from the outer side to the inner side as shown in FIG. 6. Ring-shaped member 31 that has run over locking part 33 is pulled toward the distal end side by a restoring force (a force that tends to extend in the longitudinal direction) of stent main body part 2 (cylindrical portion 21) and is locked to locking part 33. This allows stent main body part 2 to be held in a state of expanded diameter and be placed in the stenosis portion N. Thereafter, at a predetermined point, string-shaped member 32 is cut and the delivery system is removed from the body.

Biodegradable stent 1 of the present embodiment described above has the following effects.

(1) Biodegradable stent 1 includes a stent main body part 2 and a diameter expansion mechanism 3 that deforms stent main body part 2 from a state of contracted diameter to a state of expanded diameter and holds the state of expanded diameter. This diameter expansion mechanism 3 is constituted by including ring-shaped member 31; a string-shaped member, one end portion of which is connected to a proximal end side of stent main body part 2 and is inserted through ring-shaped member 31, and an other end side of which extends to a proximal end side of stent main body part 2; and locking part 33 that is disposed in the vicinity of a connecting portion between string-shaped member 32 and stent main body part 2 and is capable of locking ring-shaped member 31. Thereby, when stent main body part 2 is in a state of contracted diameter, upon pulling string-shaped member 32 toward the proximal end side of stent main body part 2, ring-shaped member 31 and locking part 33 move in approaching directions and ring-shaped member 31 and locking part 33 are engaged with each other. Therefore, since stent main body part 2 can be suitably held in a state in which the diameter is sufficiently expanded, even when the fibers constituting biodegradable stent 1 are thinned, biodegradable stent 1 having resistance to the pressure applied radially from the outside in the state of expanded diameter can be realized.

(2) Locking part 33 is constituted by first extending portion 221 constituted by forming biodegradable fiber 20 constituting stent main body part 2 in a loop shape, and one end portion of string-shaped member 32 is connected to the distal end portion of locking part 33. Thereby, upon pulling string-shaped member 32 toward the proximal end side, ring-shaped member 31 is suitably brought close to locking part 33, so that ring-shaped member 31 can be accurately locked to locking part 33.

(3) Ring-shaped member 31 is disposed on an inner side of stent main body part 2, and string-shaped member 32 is configured to include a portion extending on the inner side of stent main body part 2 on a side where the ring-shaped member 31 is disposed, a portion inserted through stent main body part 2 in the vicinity of locking part 33, and a portion extending on an outer side of stent main body part 2 on a side closer to locking part 33 than to the portion inserted through stent main body part 2. This allows ring-shaped member 31 disposed on the inner side of stent main body part 2 (cylindrical portion 21) to come out of the inner side to the outer side in the vicinity of locking part 33, and be locked so as to run over locking part 33 from the outer side to the inner side. Therefore, a force is applied by ring-shaped member 31 to locking part 33 in a direction of falling outward, but locking part 33 is prevented from falling outward because the stenosis portion N or the like is located on the outer side. As a result, the diameter expansion mechanism 3 functions more effectively.

(4) A plurality of diameter expansion mechanisms 3 are disposed at equal intervals in a circumferential direction of stent main body part 2. This allows stent main body part 2 to be uniformly expanded, when string-shaped member 32 is pulled to expand the diameter of stent main body part 2.

Although a preferred embodiment of the synthetic resin stent of the present invention has been explained, the present invention is not limited to the above-described embodiment, and can be modified as appropriate.

Figure 8:
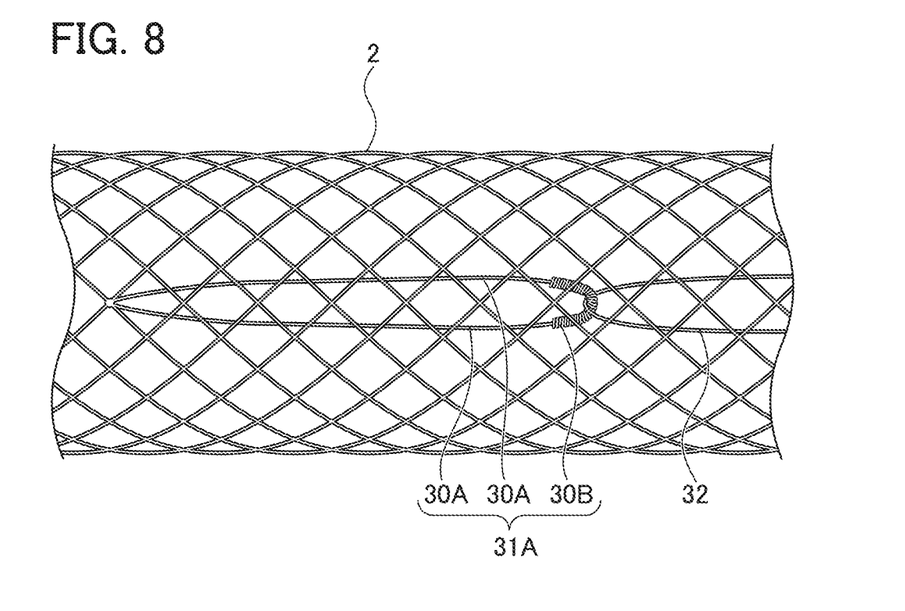
FIG. 8 is a view showing a modification of the ring-shaped member.

For example, in the present embodiment, ring-shaped member 31 is formed by rounding one fiber into a ring shape, but the present invention is not limited thereto. That is, as shown in FIG. 8, ring-shaped member 31A may be formed in a ring shape by two fibers 30A and 30A, the one end sides of which are linked to stent main body part 2, and an elastic connecting member 30B connecting the other end portions of the two fibers 30A and 30A. Elastic connecting member 30B is constituted by a metal coil formed by spirally winding a metal wire made of, for example, SUS, gold, platinum, or nickel-titanium alloy. This allows imparting elasticity to ring-shaped member 31A, so that ring-shaped member 31A can be suitably locked by locking part 33.

In FIG. 8, ring-shaped member 31A may be formed by rounding one fiber 30A in a ring shape and allowing this one fiber 30A to be inserted through elastic connecting member 30B. Elastic connecting member 30B through which fiber 30A is inserted is not limited to a metal coil, and may be a synthetic resin tube made of polyurethane or nylon.

Figure 9:
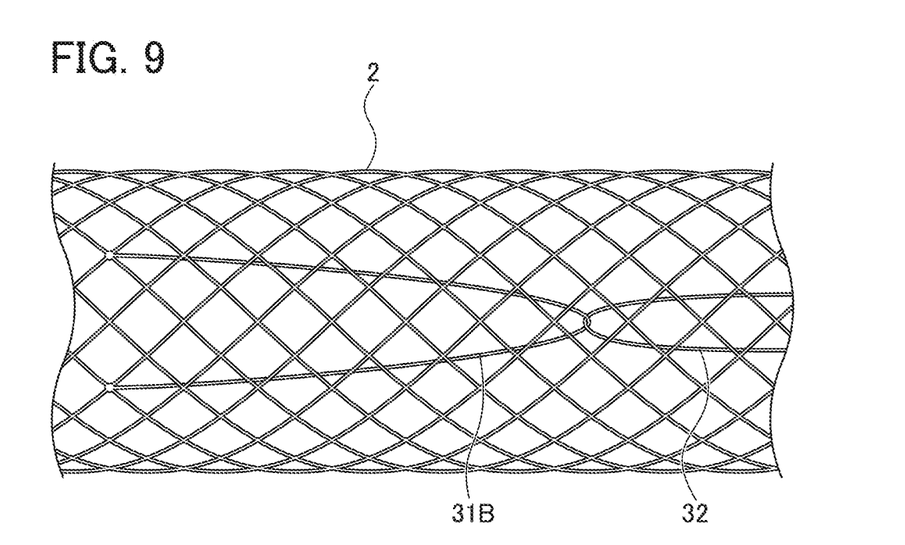
FIG. 9 is a view showing a modification of the ring-shaped member.

Further, in the present embodiment, the connecting portion between ring-shaped member 31 and stent main body part 2 is connected at one place, but the present invention is not limited thereto. That is, as shown in FIG. 9, the connecting portion between ring-shaped member 31B and stent main body part 2 may be connected at two places spaced apart in the circumferential direction of stent main body part 2. Thereby, ring-shaped member 31B can be prevented from being easily twisted, so that the operability of the diameter expansion mechanism 3 can be further improved.

Figure 10:
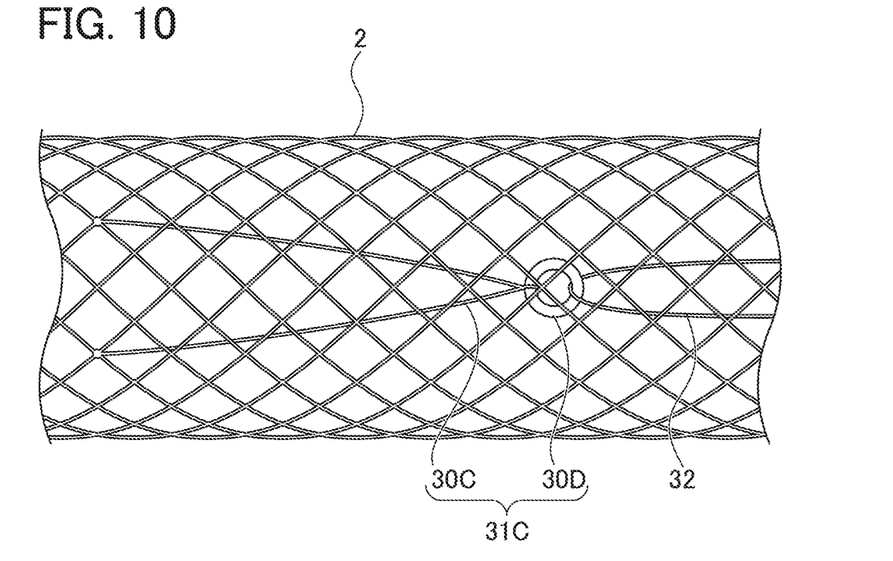
FIG. 10 is a view showing a modification of the ring-shaped member.
Figure 11:
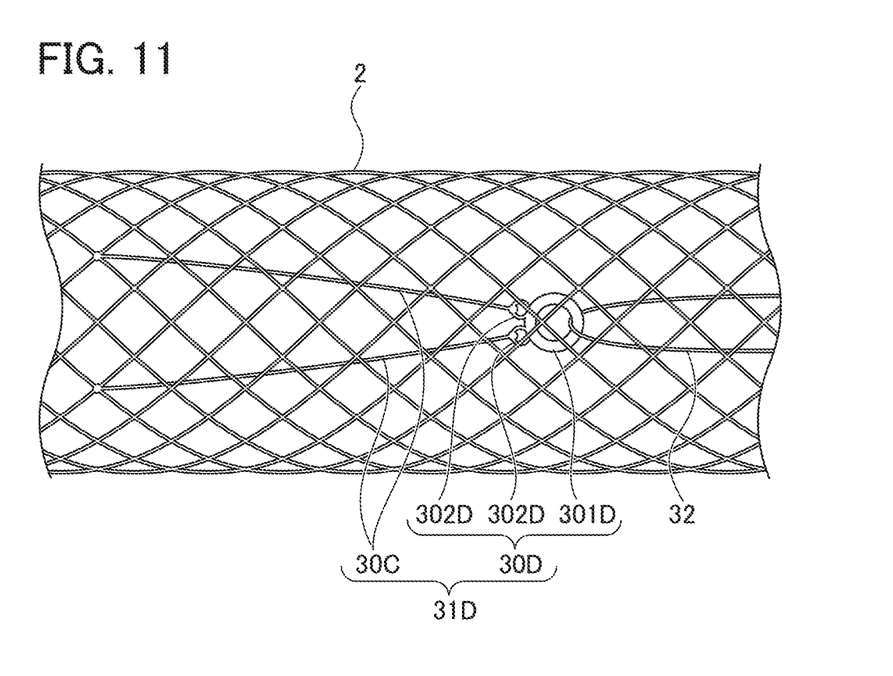
FIG. 11 is a view showing a modification of the ring-shaped member.

As shown in FIG. 10, ring-shaped member 31C may be constituted to include ring-shaped fiber 30C attached to stent main body part 2 and string-shaped member-inserting ring 30D through which fiber 30C is inserted, and string-shaped member 32 may be inserted through string-shaped member-inserting ring 30D. Further, as shown in FIG. 11, string-shaped member-inserting ring 30D may have a shape including a string-shaped member-inserting ring portion 301D through which string-shaped member 32 is inserted, and a pair of fiber-connecting portions 302D through which fibers 30C are connected or inserted.

In the present embodiment, ring-shaped member 31 is made of synthetic resin fiber or biodegradable fiber, but the present invention is not limited thereto. That is, the ring-shaped member may be formed by punching a sheet-shaped member such as a silicone sheet or a nylon sheet into a ring shape or a string shape.

Incidentally, in the present specification, the ring-shaped member refers to a member formed in an annular shape as a whole so as to be capable of being locked to locking part 33 in a state attached to stent main body part 2.

Figure 12:
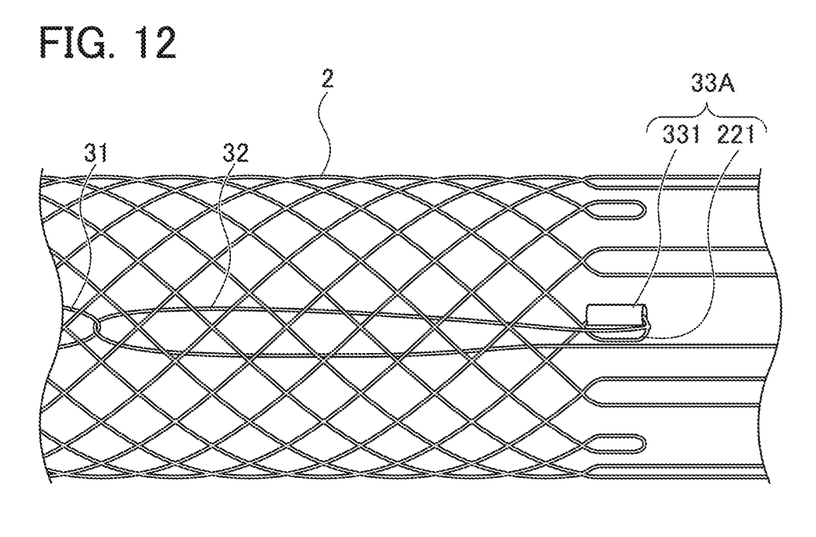
FIG. 12 is a view showing a modification of the locking part.

Further, in the present embodiment, locking part 33 is constituted by only first extending portion 221, but the present invention is not limited thereto. That is, as shown in FIG. 12, locking part 33A may be constituted to include a first extending portion 221 formed in a loop shape and a cylindrical member 331 through which biodegradable fiber 20 constituting first extending portion 221 is inserted. Since this allows locking part 33A to be configured as being difficult to deform by cylindrical member 331, ring-shaped member 31 can be suitably locked by locking part 33A.

Figure 13:
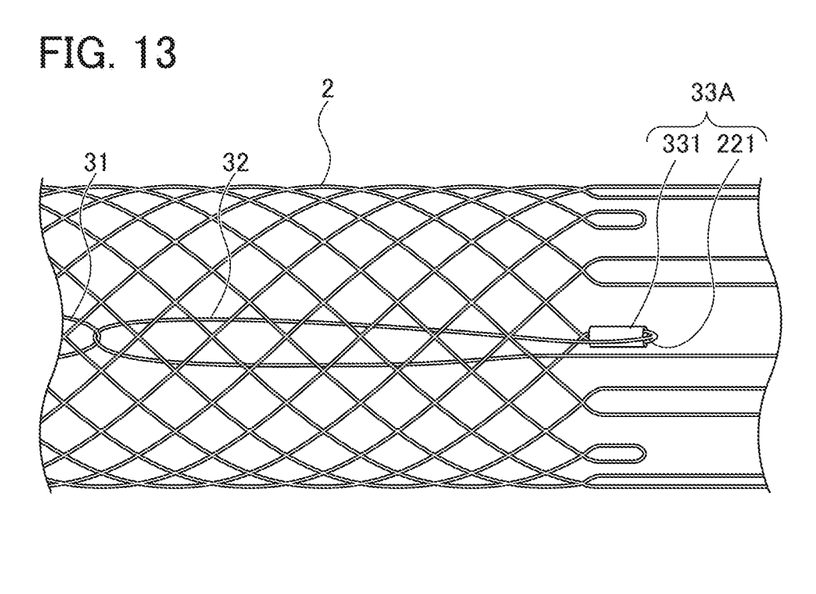
FIG. 13 is a view showing a modification of the locking part.

When locking part 33A is constituted to include first extending portion 221 and cylindrical member 331, as shown in FIG. 13, first extending portion 221 in a loop shape may be inserted through cylindrical member 331. Alternatively, first extending portion 221 to be inserted through cylindrical member 331 may not be formed in a loop shape, but the distal end portions of two biodegradable fibers 20 may be inserted through cylindrical member 331 to constitute locking part 33A.

Further, the locking part may be constituted by an extending portion formed in a loop shape and a film-shaped member (neither of which is shown) disposed so as to block the loop-shaped portion of the extension portion. Further, the locking part may be constituted without including the loop portion.

Figure 14:
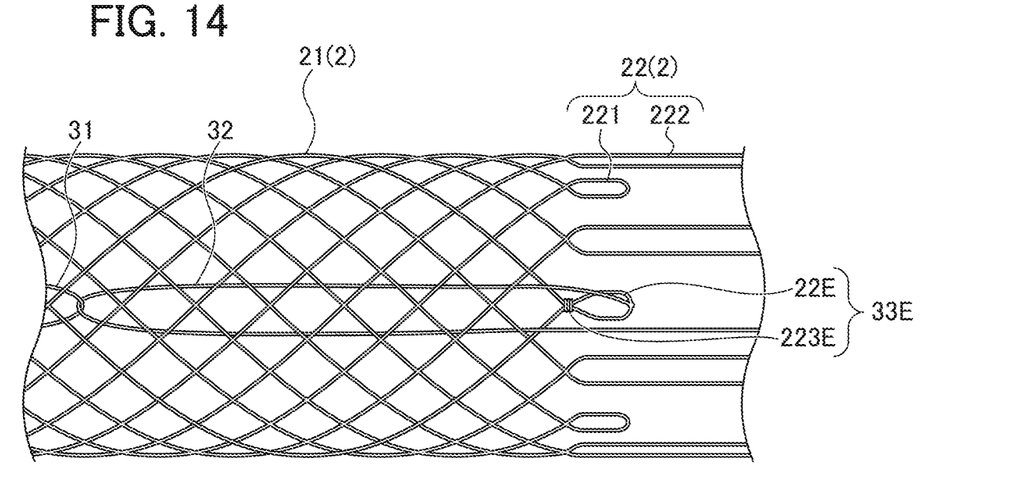
FIG. 14 is a view showing a modification of the locking part.

Furthermore, as shown in FIG. 14, locking part 33E may be constituted to include extending portion 225 formed in a loop shape and string 223E connected to the base portion (proximal end portion) of extending portion 22E. This can prevent string-shaped member 32 linked to extending portion 22E from moving from extending portion 22E toward the side of stent main body part 2.

The locking part may be formed in a loop shape using a shape memory member such as a shape memory alloy, and may be attached to the stent main body part. This allows the locking part to be restored to a desired shape and oriented in a desired direction in the state in which the biodegradable stent is placed in the stenosis portion, so that the ring-shaped member can be accurately locked by the locking part. When the locking part is constituted by a shape memory member, for example, it is preferable to make the locking part restore in the indwelling portion a shape like a shape in which the distal end portion in the loop shape is inflated, and it is preferable to make the locking part memorize a shape so that the distal end portion faces outward.

Figure 15:
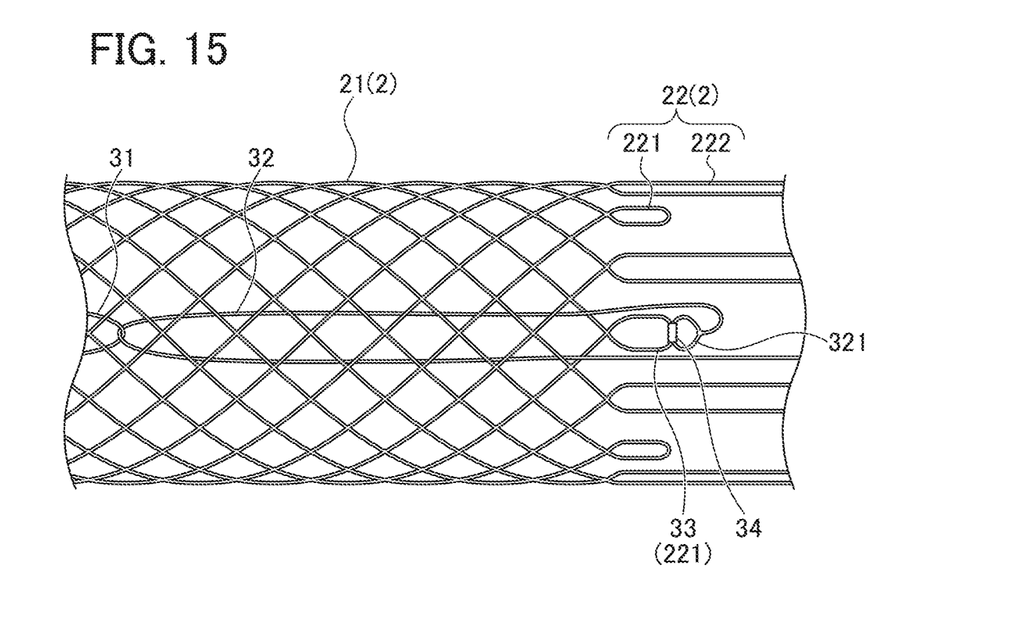
FIG. 15 is a view showing a modification of the connecting portion of the string-shaped member and the stent main body part.

In the present embodiment, one end portion of string-shaped member 32 is directly linked to stent main body part 2 (first extending portion 221), but the present invention is not limited thereto. That is, as shown in FIG. 15, the one end portion of string-shaped member 32 may be constituted to include ring-shaped portion 321, and string-shaped member 32 and stent main body part 2 may be indirectly connected via cylindrical member 34.

Further, in the present embodiment, ring-shaped member 31 is locked so as to run over locking part 33 from the outer side to the inner side, but the invention is not limited thereto. That is, the ring-shaped member may be locked so as to run over the locking part from the inner side to the outer side.

Further, in the present embodiment, string-shaped member 32 is made to pass through a mesh portion at one place, but the present invention is not limited thereto. That is, string-shaped member 32 may be made to pass through mesh portions at two or more places from the inner side to the outer side or from the outer side to the inner side.

Further, a string-shaped member may be configured without passing through a mesh portion. That is, a string-shaped member may be configured to run only on the inner side or only on the outer side of the stent main body part. In this case, when string-shaped member is pulled, string-shaped member can be prevented from being easily caught by the stent main body part.

In the present embodiment, locking part 33 is disposed at the proximal end portion of stent main body part, but the present invention is not limited thereto. That is, the locking part may be disposed on the side slightly closer to the distal end portion than to the proximal end portion of the stent main body part.

Further, in the present embodiment, locking part 33 is constituted by first extending portion 221, but the present invention is not limited thereto. That is, the locking part may be constituted by the second extending portion, and the locking part may be disposed at a different position by a portion different from the extending portion.

Figure 16:
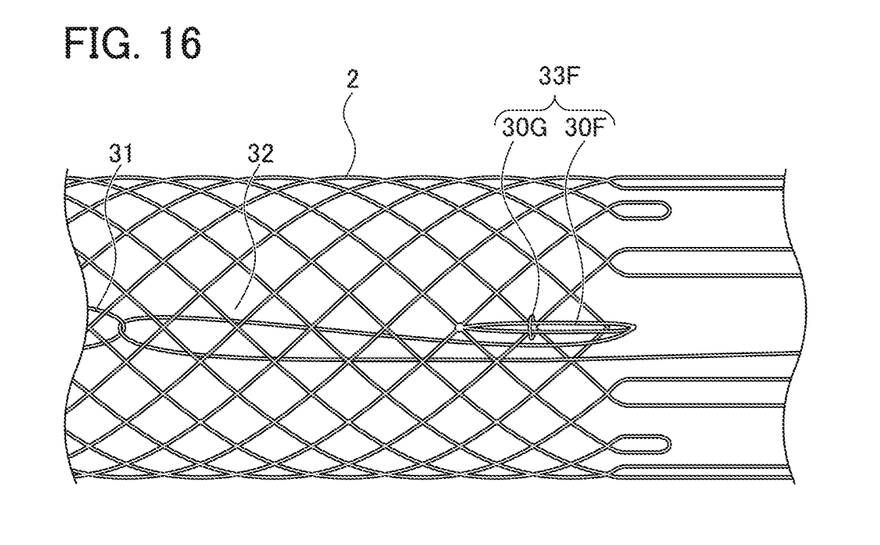
FIG. 16 is a view showing a modification of the locking part.

In the case where the locking part is disposed at a portion different from the extending portion, as shown in FIG. 16, locking part 33F may be constituted to include fiber 30F configured in a loop shape and linked to a position slightly closer to the distal end portion side than to the proximal end portion of stent main body part 2, and support ring 30G through which a fiber constituting stent main body part 2 is inserted and through which loop-shaped fiber 30F is inserted on the side closer to the proximal end of stent main body part 2 than to the connecting portion of fiber 30F with stent main body part 2. This allows locking part 33F (loop-shaped fiber 30F) to be positioned, so that the ring-shaped member can be accurately locked by locking part 33F. In addition, since support ring 30G is attached to stent main body part 2 with fibers constituting stent main body part 2 being inserted through it, the presence of support ring 30G allows locking part 33F to be positioned without hindering the diameter expansion and the diameter contraction of stent main body part 2.

In the present embodiment, ring-shaped member 31 is disposed on the inner side of stent main body part 2, but the present invention is not limited thereto. That is, the ring-shaped member may be disposed on the outer side of the stent main body part.

The size of the ring of the ring-shaped member may be any size so long as the ring can run over the locking part.

In the present embodiment, a biodegradable stent composed of biodegradable fibers is used as the synthetic resin stent, but the present invention is not limited thereto. That is, the stent may be constructed using synthetic resin fibers that do not have biodegradability.

EXPLANATION OF REFERENCE NUMERALS

1 Biodegradable stent (synthetic resin stent)
2 Stent main body part
3 Diameter expansion mechanism
31 Ring-shaped member
32 String-shaped member
33 Locking part

The invention claimed is:
1. A synthetic resin stent comprising: a stent main body part formed in a cylindrical shape by fibers made of synthetic resin and being deformable from a state of contracted diameter to a state of expanded diameter; and
a diameter expansion mechanism that is connected to the stent main body part, deforms the stent main body part from the state of contracted diameter to the state of expanded diameter and holds the stent main body part in the state of expanded diameter, wherein the diameter expansion mechanism comprises:
a ring-shaped member attached to a distal end side of the stent main body part;
a string-shaped member, one end portion of the string-shaped member being connected to a proximal end side of the stent main body part, the string-shaped member being inserted through the ring-shaped member in the state of contracted diameter of the stent main body part, an other end side of the string-shaped member extending to the proximal end side of the stent main body part; and
a locking part disposed at a connecting portion of the string-shaped member and the stent main body part or in a vicinity of the connecting portion and is capable of locking the ring-shaped member;
wherein in a state of the stent main body part being contracted, upon pulling the string-shaped member toward the proximal end side of the stent main body part, the ring-shaped member and the locking part move in approaching directions, and additionally the ring-shape member and the locking part are engaged with each other to hold the stent main body part in the state of expanded diameter.

2. The synthetic resin stent according to claim 1, wherein the locking part is configured by forming a fiber constituting the stent main body part in a loop shape, and
one end portion of the string-shaped member is connected to a distal end portion of the locking part formed in a loop shape.

3. The synthetic resin stent according to claim 1, wherein the ring-shaped member is disposed on an inner surface side of the stent main body part, and
wherein the string-shaped member has
a first portion inserted through the stent main body part in the vicinity of the locking part,
a second portion extending on an inner side of the stent main body part on a side where the ring-shaped member is disposed, and
a third portion extending on an outer side of the stent main body part on a side closer to the locking part than to the portion inserted through the stent main body part.

4. The synthetic resin stent according to claim 1, wherein a plurality of equally spaced diameter expansion mechanisms are disposed in a circumferential direction of the stent body part.

\* \* \* \* \*